United States Patent [19]

Stelting

[11] 4,230,988
[45] Oct. 28, 1980

[54] RESISTANCE NEUTRALIZING SYSTEM FOR ELECTROCHEMICAL DEVICES

[75] Inventor: Raymond B. Stelting, Needham, Mass.

[73] Assignee: Hewlett-Packard Company, Palo Alto, Calif.

[21] Appl. No.: 940,427

[22] Filed: Sep. 7, 1978

[51] Int. Cl.² .......................................... G01N 27/42
[52] U.S. Cl. .................................. 324/439; 324/425
[58] Field of Search .......... 204/195 R; 324/29, 30 R, 324/30 B, 425, 439, 446

[56] References Cited

U.S. PATENT DOCUMENTS

| | | | |
|---|---|---|---|
| 3,441,490 | 4/1969 | Johansson | 324/30 R |
| 3,710,778 | 1/1973 | Cornelius | 324/30 R |

*Primary Examiner*—Michael J. Tokar
*Attorney, Agent, or Firm*—Donald N. Timbie

[57] ABSTRACT

The net resistance of a circuit for utilizing an electrochemical cell is reduced by inserting negative resistance in the circuit that is slightly less than the inherent resistance of the cell, and means are provided for automatically adjusting the amount of negative resistance in response to the inherent resistance of the cell employed.

14 Claims, 8 Drawing Figures

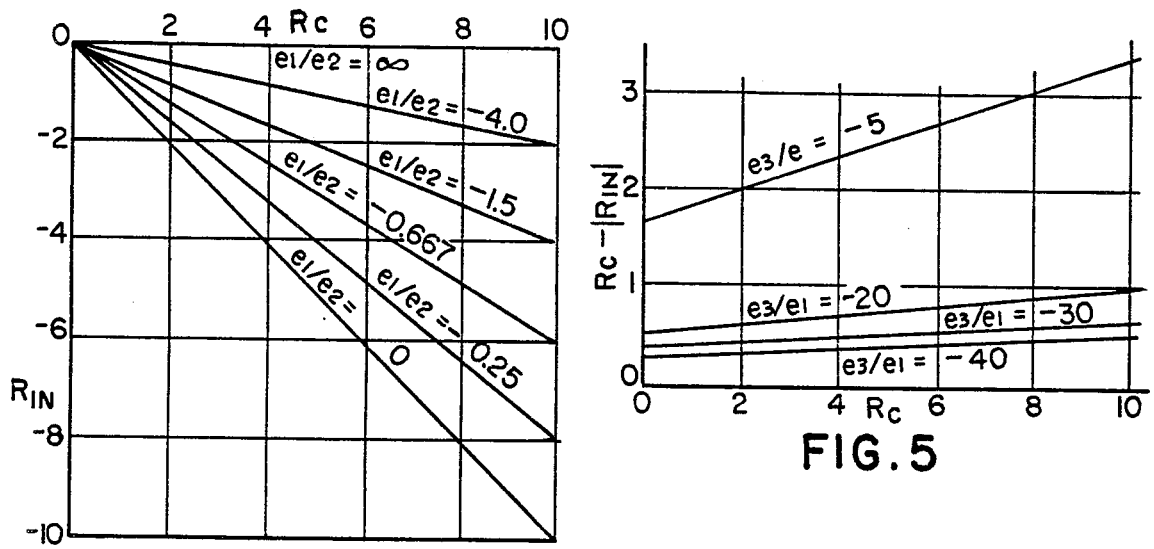
FIG. 4
FIG. 5
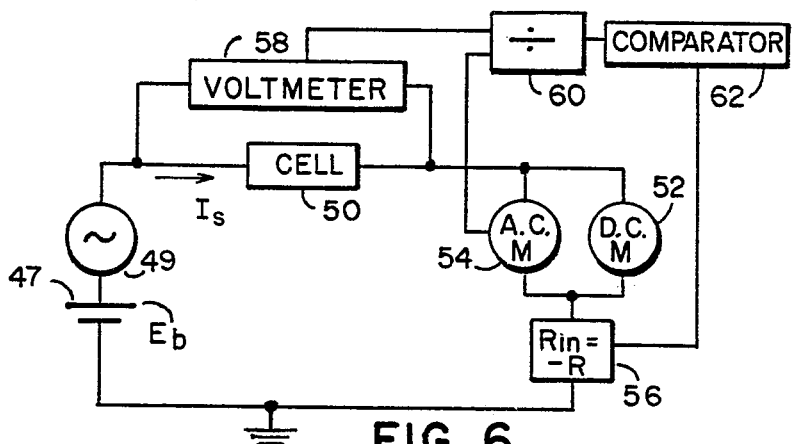
FIG. 6
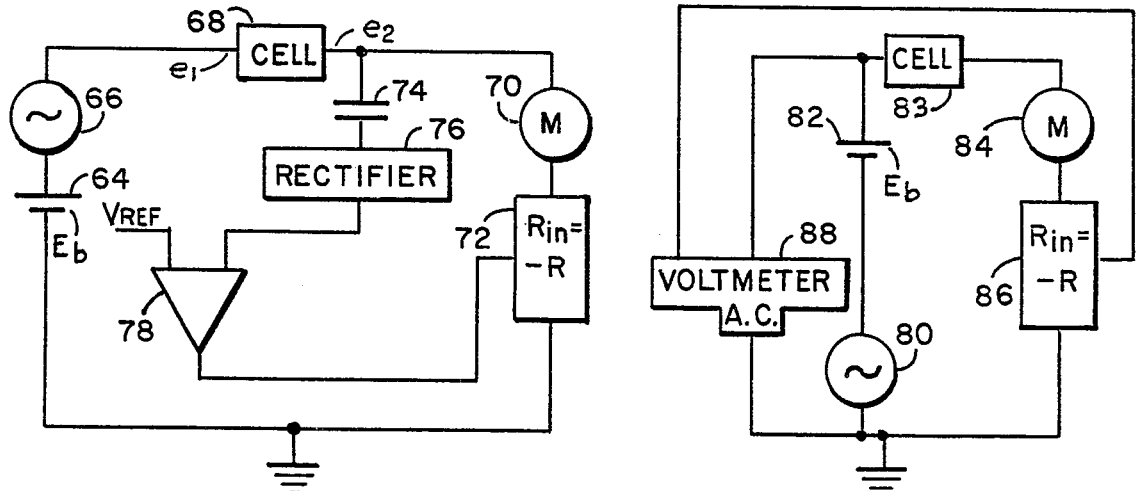
FIG. 7
FIG. 8

RESISTANCE NEUTRALIZING SYSTEM FOR ELECTROCHEMICAL DEVICES

BACKGROUND OF THE INVENTION

Electrochemical cells having a pair of electrodes separated by an electrolyte have been used to measure the concentration of gasses by applying a direct current voltage between the electrodes and measuring the current generated by the cell when gas is passed over one of its electrodes. Unfortunately, however, when the current flows through the inherent resistance of the electrodes and their associated wiring as well as the resistance of the electrolyte it produces voltage drops that can prevent the attainment of an accurate reading.

BRIEF DISCUSSION OF THE INVENTION

In order to greatly reduce the time required to obtain reasonably accurate readings, it is proposed, in accordance with this invention, that a negative resistance be inserted in the circuit so as to reduce its net resistance. Ideally, the net resistance should be the lowest possible positive value that can be attained without running the risk of net resistance being negative so as to make the circuit unstable. If all cells had the same resistance and if the resistance did not change with time, a fixed negative resistance could be employed. When it is realized, however, that a positive resistance of about one-half ohm is desired and that the resistance of some types of cells may vary from three to eight ohms, it is seen that the use of a fixed negative resistance cannot give optimum results unless a different fixed negative resistance is used for each cell.

Whereas this could be done, it is further suggested in accordance with this invention that means be provided for deriving an indication as to the inherent resistance of a cell and using that indication to adjust the value of a variable negative resistance so as to make the net resistance of the circuit a low positive value such as $+\frac{1}{2}$ ohm. This can be done by introducing a tracer signal that is affected by the inherent resistances referred to and not by other impedances such as those presented by the capacitances between the electrodes and the electrolyte. The tracer signal is used to control the amount of negative resistance.

THE DRAWINGS

Figure 3:
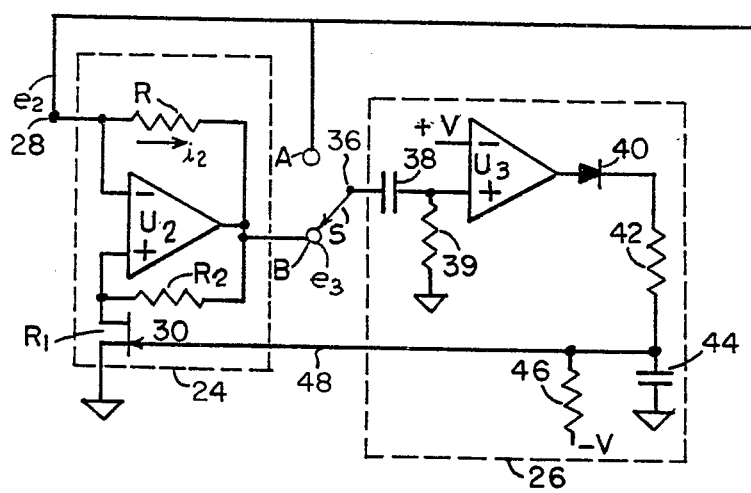
FIG. 3 is a schematic diagram of a circuit for controlling the negative resistance in response to an alternating current voltage tracer signal.

FIG. 4 includes graphs illustrating the results attained by utilizing the circuit of FIG. 3 so as to maintain a constant ratio between the amplitude of the tracer signal voltages at the input and output of an electrochemical cell;

FIG. 5 includes graphs illustrating the results attained by utilizing the circuit of FIG. 3 to maintain a constant ratio between the amplitude of the tracer signal at the output of the negative resistance converter and at the input of the electrochemical cell;

FIG. 6 is a block diagram of a system for controlling the amount of negative resistance in the circuit in response to the voltage across it and the current through it;

FIG. 7 is a block diagram of a system for controlling the amount of negative resistance in the circuit in response to the tracer voltage across the cell; and FIG. 8 is a block diagram of a system for controlling the amount of negative resistance in the circuit with a tracer signal in the form of an alternating current.

PRIOR ART

Figure 1:
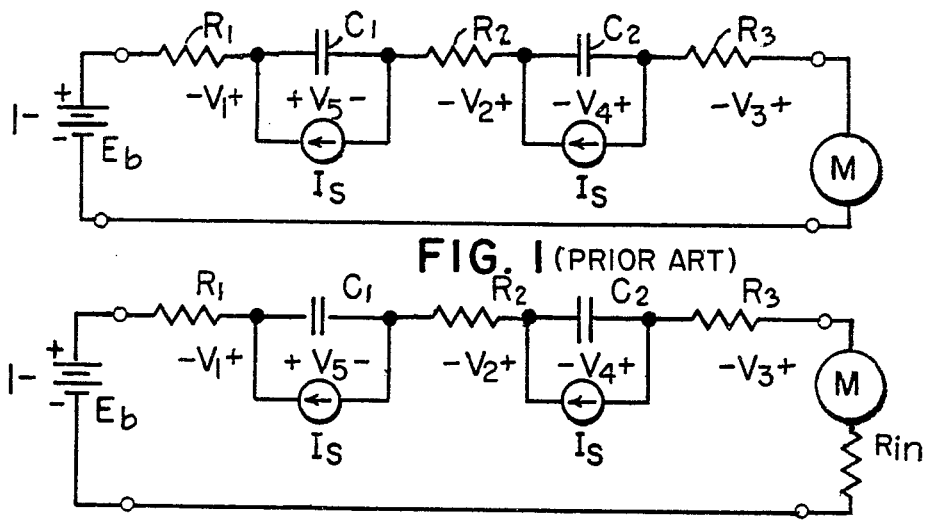
FIG. 1 is a schematic circuit utilizing an electrochemical cell in accordance with the prior art.

In the circuit of FIG. 1, a battery 1 is shown as a source of a direct current voltage $E_b$; a resistor $R_1$ represents the resistance of a first electrode and the resistance of the wire associated with it; a resistor $R_2$ represents the resistance of the electrolyte; and a resistor $R_3$ represents the resistance of a second electrode and the wire associated with it. A capacitor $C_1$ represents the capacitance between the first electrode and the electrolyte, and a capacitor $C_2$ represents the capacitance between the second electrode and the electrolyte. When, for example, CO is passed by one of the electrodes of the cell, it causes a related current $I_S$ to flow through a meter M so as to give an indication as to the concentration of CO. $V_1$, $V_2$ and $V_3$, respectively, represent the voltage drops across the resistors $R_1$, $R_2$ and $R_3$ due to a cell current $I_S$, and $V_5$ and $V_4$, respectively, represent the voltages across the capacitances $C_1$ and $C_2$.

When the concentration of the CO introduced into the cell is zero, it is assumed that $I_S$ is also zero, so that $V_1$, $V_2$ and $V_3$ are each equal to zero, and $$V_5 - V_4 - E_b = 0. \qquad (1)$$

SIMPLIFIED EMBODIMENT OF THE INVENTION

Figure 2:
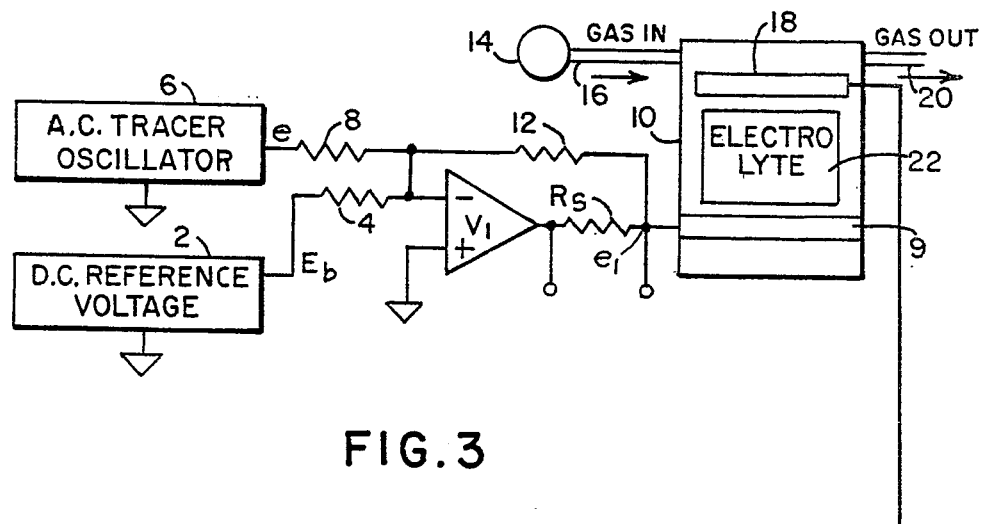
FIG. 2 is a schematic circuit illustrating the use of an electrochemical cell in accordance with the general concept of this invention.

FIG. 2 is the same as FIG. 1 with the exception of the addition of a negative resistance $R_{IN} = -R$. All other components are designated in the same way as in FIG. 1. With current $I_S$ flowing in the circuit of FIG. 2, the following relationship exists:

$$V_5 - V_4 = E_b + I_S(R_1 + R_2 + R_3 + R_{IN}) \qquad (2)$$

With $E_b$ constant, the voltages $V_5$ and $V_4$ across the capacitances between the respective electrodes and the electrolyte will change when $I_S$ changes and cause a delay in reaching a steady state value as well as inaccuracies. However, if $$R_{IN} = -(R_1 + R_2 + R_3) = -R, \qquad (3)$$

then $$V_5 - V_4 = E_b \qquad (4)$$

so that the voltages across $C_1$ and $C_2$ remain unchanged when CO is introduced into the cell.

PREFERRED FORM OF THE INVENTION

Reference is made to FIG. 3 wherein a fixed direct current voltage $E_b$ is supplied by a source 2 via a resistor 4 to the inverting input of an operational amplifier $U_1$. An alternating current tracer voltage having an amplitude, e, that is much smaller than $E_b$, is supplied via a source 6 and a resistor 8 to the inverting input of $U_1$. The non-inverting input of $U_1$ is connected to ground and its output is connected via a sensing resistor $R_S$ to a counter electrode 9 of a cell 10. A resistor 12 is connected between the end of $R_S$ remote from the output of $U_1$ to its inverting input. $U_1$ provides a direct current bias voltage to the electrode 9 and presents a low impedance at the electrode 9 for the tracer voltage signal which now has an amplitude $e_1$.

Gas having a concentration of CO, or other gas, is introduced by a pump 14 into a port 16 in the cell 10. After flowing over a sensing electrode 18 of the cell 10, the gas exits from a port 20. The electrolyte is indicated at 22.

The electrode 18 of the cell 10 is coupled to means such as the circuit within a dotted rectangle 24 for providing a negative resistance $R_{IN}$ between the electrode 18 and ground. The magnitude of this resistance is controlled by means such as the circuit shown within a dotted rectangle 26.

The circuit within the rectangle 24 is comprised of an operational amplifier $U_2$ having an inverting input connected to an input terminal 28 that is connected to the electrode 18. The tracer signal voltage at this point is $e_2$. The source-drain path of a FET 30, which provides a resistance $R_1$, is connected between the non-inverting input of $U_2$ and ground, and resistors R and $R_2$ are respectively connected between the inverting and non-inverting inputs of $U_2$ and its output. The tracer voltage has an amplitude $e_3$ at the output of $U_2$.

The particular control circuit shown within the rectangle 26 is comprised of a comparator $U_3$ having its inverting input connected to a positive direct current reference voltage $+V$ and its non-inverting input coupled to an input terminal 36 via a capacitor 38. A resistor 39 is connected between the non-inverting input of $U_3$ and ground. The output of $U_3$ is coupled to ground via a diode 40, poled as shown, a resistor 42 and a capacitor 44. A resistor 46 is connected between a point of negative direct voltage $-V$ and the junction of the resistor 42 and the capacitor 44. The voltage at this junction is coupled via a lead 48 to the gate electrode of the FET 30.

The input terminal 36 is selectively connected by a switch S to a terminal A that is connected to the electrode 18 or to a terminal B that is connected to the output of $U_2$.

OPERATION

The Negative Resistance Circuit

The negative resistance circuit 24 operates as follows. The amplitude of the alternating current voltage is e at the output of the source 6; $e_1$ at the electrode 9; $e_2$ at the electrode 18 and the terminal 28; and $e_3$ at the output of $U_2$. The current $i_2$ flowing from the terminal 28 to the output of $U_2$ is $$i_2 = \frac{e_2 - e_3}{R} \tag{5}$$

and the resistance $R_{IN}$ between the terminal 28 and ground is $$R_{IN} = \frac{e_2}{i_2} \tag{6}$$

By substitution from (5), we obtain $$R_{IN} = \frac{(e_2)(R)}{e_2 - e_3} \tag{7}$$

and therefore $$R_{IN} = \frac{R}{1 - e_3/e_2} \tag{8}$$

It is seen that $R_{IN}$ is positive for $e_3/e_2 < 1$; equal to $-R$ for $e_3/e_2 = 2$; and negative for $e_3/e_2 > 1$. From the circuit, it can be seen that $$\frac{e_3}{e_2} = \frac{R_1 + R_2}{R_1} \tag{9}$$

and for $e_3/e_2 > 1$, by substituting (9) in (8) we get $$R_{IN} = -R\frac{R_1}{R_2} \tag{10}$$

Because R and $R_2$ are fixed, the value of the negative resistance $R_{IN}$ depends on the resistance $R_1$ of the FET 30.

MAINTAINING $e_2/e_1$ CONSTANT

In a manner to be described, the control circuit 26 will maintain the peak of $e_2$ at a value of $+V$ that is applied to the inverting terminal of the comparator $U_3$ when the switch S is in contact with the terminal A. The relationship between $e_2$ and $e_1$ is given by the expression $$\frac{e_2}{e_1} = \frac{R_{IN}}{R_{IN} + R_c} = \frac{1}{1 + R_c/R_{IN}} \tag{11}$$

wherein $R_c$ is the total resistance of the cell 20 or equal to $R_1 + R_2 + R_3$ of FIGS. 1 and 2. Thus, if $e_2/e_1$ is held constant for various cell resistances $R_c$ by adjusting the value of $R_{IN}$, $R_{IN}$ will be a constant percentage of $R_c$ so as to yield relationships illustrated by the graphs of FIG. 4. Suppose, for example, that the resistance $R_c$ of a particular cell is 5 ohms and that $e_2/e_1 = -\frac{1}{4}$ or $e_1/e_2 = -4$. The value of $R_{IN}$ would be $-1$ ohm and the total resistance, $R_{IN} + R_c$, in the circuit would be 4 ohms. The total resistance would be reduced to 1 ohm if $e_1/e_2$ were made equal to $-\frac{1}{4}$ or $e_2/e_1 = -4$. Thus, the total resistance decreases as $e_2/e_1$ increases, but it will not be the same for all values of $R_c$, e.g., with the $e_2/e_1$ again $= -4$, and $R_c = 10$ ohms, $R_{IN}$ will be $-8$ ohms and the total resistance of the circuit will be 2 ohms. Whereas this is a useful mode of operation, better results are attained if $e_3/e_1$ is held constant.

MAINTAINING $e_3/e_1$ CONSTANT

With the switch S of FIG. 3 in contact with the terminal B, the control circuit 26 will keep the peak of $e_3$ at the value of $+V$ applied to the inverting terminal of $U_3$ so that $e_3/e_1$ will be constant. By rearrangement of the terms of equation (8), it becomes $$\frac{e_3}{e_2} = 1 - \frac{R}{R_{IN}} \tag{12}$$

By substituting the expression for $e_2$ from equation (11) into equation (12), we obtain $$\frac{e_3}{e_1} = \frac{R_{IN} - R}{R_{IN} + R_c} \quad (13)$$

Solving (13) for $R_{IN}$ yields $$R_{IN} = \frac{-(e_3/e_1) R_c - R}{e_3/e_1 - 1} \quad (14)$$

The total circuit resistance is relatively independent of the value of $R_c$ as shown by the graph in FIG. 5 for relatively large negative values of $e_3/e_1$. Note also that for $R_c = 5.5$ ohms, the total circuit resistance is $+0.5$ ohms and that as $R_c$ varies over an expected range of values, the total circuit resistance does not vary much from the $+0.5$ ohm value. As the ratio of $e_3/e_1$ is increased by increasing the value of $+V$ at the inverting input of $U_3$, the total resistance becomes less. When the ratio of $e_3/e_1$ is reduced to $-5$, the value of the total circuit resistance $R_{IN} + R_c$ is much greater and varies by a larger percentage.

THE CONTROL CIRCUIT 26

Because of the capacitor 38, the control circuit 26 responds only to the alternating current tracer voltage in setting the value of $R_{IN}$. If no tracer signal voltage is applied to the terminal 36, the output of $U_3$ is in its negative or low state and is of such value with respect to $-V$ that the diode 40 is cut off. Under this condition, the resistance $R_1$ of the FET 30 is large, and, as can be seen from equation (10), this makes $|R_{IN}|$ large. This, in turn, makes both $e_2$ and $e_3$ large. When the switch S is in contact with the terminal A, the tracer signal voltage $e_2$ is applied to the non-inverting input of the comparative $U_3$, and when the switch S is in contact with the terminal B, the tracer signal voltage $e_3$ is applied to the non-inverting input of $U_3$. In either case, when the amplitude of the tracer signal voltage exceeds the value of $+V$, the output of $U_3$ shifts to its positive state. The diode 40 now conducts and charges the capacitor 44 in the positive direction. This reduces the value of $R_1$, the value of $|R_{IN}|$ and consequently the value of the tracer signal voltage, whether it is $e_2$ or $e_3$, until the amplitude of the tracer signal voltage applied to the non-inverting input of $U_3$ equals the value of $+V$. The voltage $+V$ is set at a fraction of the maximum amplitude of whichever of $e_2$ or $e_3$ is being used. That $e_2/e_1$ can exceed unity arises from the fact that $R_{IN}$ is negative. That $|e_3/e_1|$ can be greater than unity, i.e., up to a value such as 30, can be seen from equation (9) which defines the gain of the negative resistance circuit 24.

Electrode electrolyte interface voltages must be held very nearly constant in order for cells of this type to accurately detect and measure gas concentration. For a full-scale current $I_S$ of 15 ma, a cell having a resistance, $R_c$, of 5.5 ohms would produce an 87.5 mv change in the voltage across the capacitances $C_1$ and $C_2$ if this invention were not used, but when, for example, the circuit is used so as to make the total circuit resistance $R_{IN} + R_c$ equal to 0.5 ohm, the voltage across the capacitances $C_1$ and $C_2$ would be reduced to 7.5 mv, thus improving accuracy and speeding up the response.

GENERAL COMMENT

The value of either $e_2$ or $e_3$ of FIG. 3 is affected by or indicative of the value of the resistance $R_c$ of the cell 10 and the negative resistance circuit 24, and the control circuit 26 respond to either $e_2$ or $e_3$ to reduce the total resistance $R_c + R_{IN}$. Whereas the particular circuit of FIG. 3 performs in a highly satisfactory manner, it will be apparent to those skilled in the art that other circuits could be used. A few general examples follow.

Reference is made to FIG. 6 wherein a battery 47 and a source 49 of alternating current tracer voltage are connected in series between ground and an input of an electrochemical cell 50. The output of the cell 50 is connected via a direct current ammeter 52 and an alternating current ammeter 54 that is in parallel with the ammeter 52 to the input of a device 56 that can be controlled so as to vary the value of a negative resistance $R_{IN}$.

The device 56 is controlled as follows. An alternating current voltmeter 58 is connected in parallel with the cell 50 and provides an output representing the voltage drop across the resistance $R_c$ of the cell 10 caused by current $I_S$ produced in the circuit by the source 49 of alternating current tracer signal voltage $e_1$. The alternating current ammeter 54 provides a signal representing the value of the alternating current. A divider 60 that is coupled to the voltmeter 58 and the ammeter 54 produces a signal indicative of the resistance $R_c$ of the cell 50. A comparator 62 responds to this signal to control the value of negative resistance provided by the device 56.

In FIG. 7, a battery 64 and a source 66 of alternating current tracer voltage are connected in series between ground and an input of an electrochemical cell 68. Its output is connected to ground via a direct current ammeter 70 in series with a means 72 for providing controllable amounts of negative resistance $R_{IN}$. The tracer signal voltage $e_2$ at the output of the cell 68 is coupled via a capacitor 74 to a rectifier 76. Inasmuch as $e_1$ is constant, the voltage $e_2$ is determined by the value of the cell resistance $R_c$ and the value of the negative resistance $R_{IN}$. The voltage at the output of the rectifier 76 is compared in a comparator 78 with a reference voltage $V_{ref}$. Whenever the rectified voltage is greater than $V_{ref}$, the output of the comparator 78 is such as to change $R_{IN}$ as required.

Instead of using a tracer signal that is an alternating voltage, an alternating current can be used as illustrated in FIG. 8. A source 80 of alternating current tracer signal is connected in series with a battery 82 between ground and an input of an electrochemical cell 83. Its output is connected to ground by a direct current ammeter 84 connected in series with a device 86 for providing a controllable amount of negative resistance. An alternating current voltmeter 88 is connected in shunt with the series circuit formed by the battery 82 and the source 80. If the net resistance $R_c + R_{IN}$ is a desired value, the output of the voltmeter 88 will be a predetermined value. If it departs from this value because of a change in the resistance $R_c$ of the cell 83, it can be used to adjust the value of $R_{IN}$. Other types of tracer signals may be used but they must produce a different response in the resistors of a cell and the capacitances therein.

I claim:

1. Apparatus for measuring the concentration of a gas, comprising an electrochemical cell having first and second electrodes and arranged to contain an electrolyte between said electrodes, said cell having resistance associated with each of its electrodes and its electrolyte when the electrolyte is present in the cell and capacitance between each electrode and the electrolyte when the electrolyte is present in the cell, a source of direct current potential, means providing negative resistance, means connecting said cell, said source of direct current potential and said means for producing negative resistance in a circuit, and means for measuring direct current flowing in said circuit.

2. Apparatus as set forth in claim 1 wherein a source of tracer signal is coupled to said circuit so as to make an alternating current flow therein whereby said alternating current produces a voltage drop across the resistance significantly larger than the voltage drop it produces across said capacitance, and means responsive to the voltage drop produced across said resistance by said alternating current for varying the value of negative resistance provided by said means.

3. Apparatus as set forth in claim 2 wherein said source of tracer signal provides alternating current voltage in series with the electrodes of said cell.

4. Apparatus as set forth in claim 1 wherein said means providing a negative resistance is comprised of an operational amplifier having an inverting input connected to a first point, a non-inverting input and an output, a resistor connected between the inverting input of said amplifier and its output, means providing a first resistance between the non-inverting input of said amplifier and a second point, a second resistor connected between the non-inverting input of said amplifier and its output, and said first and second points being connected in said circuit so that current flowing in said circuit flows between them.

5. Apparatus as set forth in claim 4 wherein said means providing said first resistance is such that the resistance it provides can be varied, and wherein means are provided for varying the resistance.

6. Apparatus as set forth in claim 2 wherein said means providing a negative resistance is comprised of an operational amplifier having an inverting input connected to a first point, a non-inverting input and an output, a resistor connected between the inverting input of said amplifier and its output, means providing a first resistance between the non-inverting input of said amplifier and a second point, a second resistor connected between the non-inverting input of said amplifier and its output, said first and second points being connected in said circuit so that current flowing in said circuit flows between them, and wherein said means for varying the values of said negative resistance operates by changing the value of said first resistance.

7. A system for neutralizing the effect of resistance associated with an electrochemical cell comprising an electrochemical cell having first and second electrodes and an electrolyte between them, said electrodes and said electrolyte each having a given resistance, there being capacitance between each electrode and said electrolyte, a source of direct current voltage connected between one of said electrodes and ground, an operational amplifier having an inverting input, a non-inverting input and an output, a connection between the inverting input and the other of said electrodes, a resistor connected between said inverting input of said amplifier and its output, means providing a variable first resistance connected between the non-inverting input of said amplifier and ground so as to form a circuit, means providing a second resistance connected between the non-inverting input of said amplifier and its output, means for measuring any direct current flowing in said circuit, means for causing an alternating tracer current to flow in said circuit, and control means for varying the value of said first resistance as a function of the voltage drop produced by said tracer current across the given resistances of said cell.

8. A system as set forth in claim 6 wherein said control means varies the value of said first instance so as to keep the voltage produced by the alternating tracer current at said other electrode of said cell at a constant value.

9. A system as set forth in claim 6 wherein said control means varies the value of said first resistance so as to keep the voltage produced by the alternating tracer current at the output of said operational amplifier at a constant value.

10. Apparatus for measuring the concentration of a gas, the apparatus comprising an electrochemical cell having first and second electrodes and arranged to contain an electrolyte between the electrodes, the cell having resistance associated with each of its electrodes and capacitance between each electrode and the electrolyte when the electrolyte is present in the cell, means providing negative resistance, terminals between which a source of potential may be connected, means for connecting the electrodes of the cell, the negative resistance and said terminals in a series circuit, and means for measuring any direct current flowing in said circuit.

11. Apparatus as set forth in claim 10 wherein a source of tracer signal is coupled to said circuit so as to make an alternating current flow therein whereby said alternating current produces a voltage drop across the resistance significantly larger than the voltage drop it produces across said capacitance, and means responsive to the voltage drop produced across said resistance by said alternating current for varying the value of negative resistance provided by said means.

12. Apparatus as set forth in claim 10 wherein said means providing a negative resistance is comprised of an operational amplifier having an inverting input connected to a first point, a non-inverting input and an output, a resistor connected between the inverting input of said amplifier and its output, means providing a first resistance between the non-inverting input of said amplifier and a second point, a second resistor connected between the non-inverting input of said amplifier and its output, and said first and second points being connected in said circuit so that current flowing in said circuit flows between them.

13. Apparatus as set forth in claim 10 wherein said means providing said first resistance is such that the resistance it provides can be varied, and
wherein means are provided for varying the resistance.

14. Apparatus as set forth in claim 11 wherein said means providing a negative resistance is comprised of
an operational amplifier having an inverting input connected to a first point, a non-inverting input and an output,
a resistor connected between the inverting input of said amplifier and its output,
means providing a first resistance between the non-inverting input of said amplifier and a second point,
a second resistor connected between the non-inverting input of said amplifier and its output,
said first and second points being connected in said circuit so that current flowing in said circuit flows between them, and
wherein said means for varying the values of said negative resistance operates by changing the value of said first resistance.

* * * * *